United States Patent [19]

O'Brien et al.

[11] 4,017,301
[45] Apr. 12, 1977

[54] PLANT GROWTH REGULANTS

[75] Inventors: John B. O'Brien, Watertown, Conn.; John Pisanchyn, Morristown, N.J.; S. Robert Colby, Durham, N.H.

[73] Assignee: Allied Chemical Corporation, Morris Township, N.J.

[22] Filed: Jan. 14, 1975

[21] Appl. No.: 540,937

Related U.S. Application Data

[62] Division of Ser. No. 387,054, Aug. 9, 1973, Pat. No. 3,873,301.

[52] U.S. Cl. ................................. 71/118
[51] Int. Cl.² ........................... A01N 9/20
[58] Field of Search ............... 71/118, 76, 106, 113

[56] References Cited

UNITED STATES PATENTS

| | | | |
|---|---|---|---|
| 2,636,816 | 4/1953 | Stewart | 71/118 |
| 3,087,805 | 4/1963 | Metivier | 71/118 |
| 3,148,049 | 9/1964 | Herschler | 71/106 |
| 3,515,536 | 6/1970 | Hill et al. | 71/121 |
| 3,766,270 | 10/1973 | Hiller et al. | 71/118 |

FOREIGN PATENTS OR APPLICATIONS

| | | | |
|---|---|---|---|
| 1,916,054 | 10/1970 | Germany | 71/113 |

OTHER PUBLICATIONS

Pisanchyn et al., "Lysine Alkyl Esters" (1971) CA 75 No. 21009y, (1971).
Sayles et al., "New Synthetic Methods for etc.," (1949) JACS 71 pp. 3161–3164 (1949).

*Primary Examiner*—Glennon H. Hollrah
*Attorney, Agent, or Firm*—Jack B. Murray, Jr.; Arthur J. Plantamura; Ernest A. Polin

[57] ABSTRACT

A method of improving the yield of plants such as legumes by the application thereto of plant growth regulants comprising nitro-oximino alkanoic acids and derivatives thereof having the general formula:

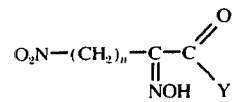

wherein $n$ is an integer from 1 to 12 and wherein Y is selected from the group consisting of OR, SR, NRR' in which R and R' are independently selected from the group consisting of hydrogen, alkyl, cycloalkyl, alkaryl, aralkyl, aryl, heterocyclic, alkenyl and alkynyl, and OR'' in which R'' is an alkali metal.

8 Claims, No Drawings

PLANT GROWTH REGULANTS

This is a division of application Ser. No. 387,054, filed Aug. 9, 1973, now U.S. Pat. No. 3,873,301.

FIELD OF THE INVENTION

This invention relates to compounds having a growth regulating effect when applied to plants. The compounds disclosed are of particular value for increasing the yield per plant and per acre of agronomic crops, such as legumes.

SUMMARY OF THE INVENTION

The yield of certain plants, particularly agronomic crops such as legumes, can be improved advantageously by applying to the plants an effective amount of one or more of the plant growth regulants described below.

By the application of these growth regulants to crops such as legumes, the yield per plant as well as the yield per acre may be improved ten percent or more as compared to untreated control plantings. The number of the fruit and seed is increased by the application of these growth regulants. Moreover, the plant height of the plants is decreased by the application of the growth regulants, thereby causing the plants to remain upright and preventing yield loss which occurs during the harvesting of taller untreated plants which tend to lean over close to the ground, a condition termed "lodging".

DETAILED DESCRIPTION OF THE INVENTION

The plant growth regulants of the present invention are nitro-oximino alkanoic acids and derivatives thereof having the general formula:

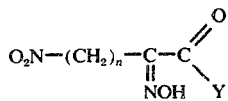

wherein $n$ is an integer from 1 to 12 and Y is selected from the group consisting of OR, SR, NRR' in which R and R' are independently selected from the group consisting of hydrogen, alkyl, cycloalkyl, aralkyl, alkaryl, aryl, heterocyclic, alkenyl and alkynyl, and OR'' in which R'' is alkali metal.

The alkyl group generally contains from 1 to 12 carbon atoms and preferably contains from 1 to 5 carbon atoms. Examples of such alkyl groups are: methyl, ethyl, pentyl, octyl and dodecyl. The cycloalkyl group generally contains from 3 to 12 carbon atoms and preferably contains from 3 to 6 carbon atoms. Examples of such groups are cyclobutyl, cyclohexyl and cyclooctyl. The aralkyl group generally consists of phenyl or alkyl substituted phenyl as the aryl substituent and an alkyl substituent having from 1 to 12 carbon atoms and preferably from 1 to 6 carbon atoms. Examples of such aralkyl groups are: benzyl, o-ethylbenzyl, 5-phenylpentyl and 6-phenyldodecyl. The alkaryl group generally consists of phenyl or tolyl as the aryl substituent and an alkyl substituent having from 1 to 12 carbon atoms and preferably from 1 to 6 carbon atoms. Examples of such alkaryl groups are: tolyl, m-ethylphenyl, o-ethyltolyl and m-hexyltolyl. The aryl group is generally phenyl. The alkali metal is typically sodium potassium or lithium. Heterocyclic groups such as thienyl, pyridyl and piperidyl may be employed. In addition, the moiety —NRR' may comprise a heterocyclic group such as

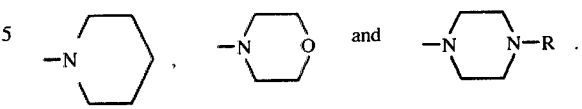

The alkenyl group generally contains from 3 to 12 carbon atoms and preferably from 3 to 5 carbon atoms. Examples of such alkenyl groups are propenyl, butenyl and decenyl. The alkynyl group generally contains from 3 to 12 carbon atoms and preferably from 3 to 5 carbon atoms. Examples of such alkynyl groups are propynyl, hexynyl and decynyl.

Examples of plant growth regulants of the present invention wherein Y of the above general formula is OR or SR in which R is hydrogen, alkyl, cycloalkyl, aralkyl, alkaryl, aryl, hetero-cyclic, alkenyl or alkynyl are octyl 12-nitro-2-oximinododecanoate, dodecyl 10-nitro-2-oximinodecanoate, octyl 6-nitro-2-oximinohexanoate, cyclohexyl 6-nitro-2-oximinohexanoate, cyclooctyl 10-nitro-2-oximinodecanoate, benzyl 6-nitro-2-oximinohexanoate, benzyl 12-nitro-2-oximinododecanoate, m-cresyl 8-nitro-2-oximinooctanoate, phenyl 5-nitro-2-oximinopentanoate, m-tolyl 3-nitro-2-oximinopropanoate, o-ethylbenzyl 4-nitro-2-oximinobutanoate, m-isobutybenzyl 10-nitro-2-oximinodecanoate, 2-thienyl 6-nitro-b 2-oximinohexanoate, 2-pyridyl 12-nitro-2-oximinododecanoate, 2-pyridyl 11-nitro-2-oximinoundecanoate, 2-propenyl 6-nitro-2-oximinohexanoate, 2-decenyl 8-nitro-2-oximinooctanoate, 1-butenyl 7-nitro-2-oximinoheptanoate, 2-propynyl 6-nitro-2-oximinohexanoate, 2-decenyl 10 -nitro-2-oximinodecanoate, 2-hexenyl 12-nitro-2-oximinododecanoate, -pyridyl 12-nitro- methyl 6-nitro-2-oximinohexanoate, ethyl 6-nitro-2-oximinohexanoate, 6-nitro-2-oximinohexanoic acid, 10-nitro-2-oximinodecanoic acid, pentyl 8-nitro-2-oximinothiooctanoate and m-tolyl 4-nitro-2-oximino-thiobutanoate.

When Y in the general formula is NRR' in which R aND R' are as defined above, examples of nitro-oximino alkanoic acid derivatives which may be used as plant growth regulants are N-ethyl 6-nitro-2-oximinohexanamide, N-decyl 12-nitro-2-oximinodecanamide, N-cyclohexyl 3-nitro-2-oximinopropanamide, N-benzyl 6-nitro-2-oximinohexanamide, N-(m-tolyl) 5-nitro-2-oximinopentanamide, N-(2-thienyl) 7-nitro-2-oximinoheptanamide, N-(2-decenyl) 8-nitro-2-oximinooctanamide, N-(2-hexynyl) 12-nitro-2-oximinodecanamide, N,N-diethyl 6-nitro-2-oximinohexanamide, N,N-dibenzyl 8-nitro-2-oximinooctanamide, N,N-di(m-thienyl) 10-nitro-2-oximinodecanamide, 8-nitro-2-oximinooctanamide and 6-nitro-2-oximinohexanamide.

Examples of nitro-oximino alkanoic acid derivatives when Y in the general formula is OR'' are sodium 6-nitro-2-oximinohexanoate, potassium 10-nitro-2-oximinodecanoate, and lithium 7-nitro-2-oximinoheptanoate.

Plant growth regulants which are especially preferred are methyl 6-nitro-2-oximinohexanoate, ethyl 6-nitro-2-oximinohexanoate, 6-nitro-2-oximinohexanamide and 6-nitro-2-oximinohexanoic acid.

The plant growth regulants of the present invention are known and may be prepared by conventional methods. For example, ethyl 6-nitro-2-oximinohexanoate which is disclosed in Sayles and Degering, New Synthetic Methods For The Preparation of Lysine, J. Amer. Chem. Soc. 3161, 3162–3163 (1949) may be prepared by the reaction of ethyl 2-acetyl-6-nitrohexanoate with n-butyl nitrite. 6-Nitro-2-oximinohexanamide is prepared by the reaction of 2-nitro-6-oximinocyclohexanone with anhydrous ammonia as disclosed in U.S. Pat. application Ser. No. 97,290 filed Dec. 11, 1970 by Fuhrmann et al., entitled: "Ammonolysis of 2-nitro-6-oximino cyclohexanone". 6-Nitro-2-oximinohexanoic acid is prepared as described in B. F. Burrows and W. B. Turner, J. Chem. Soc. (C) 255,259 (1969).

The plant growth regulants of the present invention are applied as compositions prepared by admixing one or more of the plant growth regulants of the present invention as the active ingredient in plant growth regulative effective amounts with a material of the kind used and referred to in the plant growth regulant art as an inert carrier or diluent in order to provide formulations adapted for ready and efficient application to plants (i.e., crop plants such as legumes) using conventional applicator equipment. In other words, the active ingredient is mixed with an additional material or materials of a kind known in the art to provide a formulation adapted for ready application by conventional means such as through suitable jets, nozzles, spreaders and similar devices.

It is preferred that the compositions contain active ingredient in a concentration of between about 10 and 3000 ppm by weight, and most preferably between about 100 and 1000 ppm by weight. In the case of legumes such as a soybean crop having plants spaced four to the foot in 30 inch rows, less than about eight pounds, and preferably between 0.025 and 4.0 pounds, of the active ingredient may be applied per acre, in order to effect the desired plant growth regulation.

Application of more than about eight pounds of active ingredient per acre to such plants tends to produce an undesired phytotoxic effect upon the plants. Application of less than about 0.025 pound of active ingredient per acre tends to become uneconomical since repeated applications become necessary in order to achieve the desired growth regulation.

The compositions containing the plant growth regulants may be prepared in the form of a solid or liquid such as a solution, emulsion, suspension, wettable powder, granules, pellets or dust according to the intended use. Solid compositions, for example, may be prepared in the form of wettable powders and are compounded to give homogenous free-flowing powders by milling or admixing the active ingredient with finely divided solids, such as clay, fuller's earth, diatomaceous earth, charcoal, chalk and the like, together with wetting and dispersing surface-active agents. Solid compositions may also be in the form of dust formulations which may be prepared by mixing or blending the active ingredient with a finely divided solid carrier as indicated above, or the active ingredient may be impregnated on or incorporated into granules or pellets.

Where liquid compositions are prepared as solution, emulsion or suspension, such compositions may also be conveniently prepared as concentrates containing about 5 to 30 percent by weight of active ingredient which can be diluted in the field with a suitable non-phytotoxic solvent prior to use. Examples of suitable non-phytotoxic solvents include acetone, dimethylformamide, methanol, or mixtures thereof, in addition to water. Such liquid compositions also preferably contain a surface-active agent, that is, an emulsifying agent.

The surface-active agents employed with the solid or liquid compositions serve to improve wetting, thus ensuring good delivery of the active ingredient to all parts of the plant and preventing build-up of high concentrations of active ingredient on the foliage which might produce leaf burn. These surface-active agents can be of the anionic, cationic or non-ionic type. Such compounds can be found listed by J. B. McCutcheon in "Soap and Chemical Specialties" for December, 1957 and January, February, March and April of 1958. In addition, surfactants such as Tween-20 (tradename for a series of polyoxyethylene derivatives of fatty acid partial esters of sorbitol anhydrides) may also be employed. Generally, the surface-active agent will not comprise more than about 1 to 10 percent by weight of the formulation.

The effectiveness of the application is particularly enhanced if there is also incorporated into the composition a sticking agent. The sticking agent serves to increase the retention time of the active ingredient on the foliage, thereby reducing the number of applications required to achieve the desired plant growth regulation. Non-phytotoxic sticking agents, such as a readily emulsified oxidized polyethylene wax as in U.S. Pat. No. 2,976,210 (issued in 1961 to Cosby et al.), may be employed in an amount ranging from about 0.1 to 1.0 pound per 100 pounds of composition.

While increased yield of soybean crops can be effected by a single application of the plant growth regulants of this invention, two or more applications may be made and are particularly advantageous if rain follows the first or subsequent application. The most convenient means of applying the growth regulants is spraying by airplane. In areas where aerial spraying is impractical, however, the compositions can be effectively sprayed from trucks or with hand spraying equipment.

It has been further discovered that the application of the nitro-oximino alkanoic acids and their derivatives to plants producing ornamental flowers, such as chrysanthemums, effects both a decreased plant height and an increased flower size and thereby provides a more full, compact plant having an aesthetic appearance superior to chrysanthemums generally available in the market.

This invention may be further illustrated by reference to the following examples.

EXAMPLE 1

Several acres of an Arkansas field are sown with soybean plants (Davis) such that the plants when mature are spaced about four plants per foot in rows separated by about 30 inches. A concentrate is prepared by dissolving 280 grams of ethyl 6-nitro-2-oximinohexanoate in 1240 milliliters of a solvent having the volume percent composition: 18% acetone and 82% water. This concentrate is then diluted with water in the field to 40 gallons. To this solution is added 0.1 percent by weight of Tween-20 spreading agent.

This solution is evenly applied as a spray to foliage on one acre of the soybean plants at the early flowering stage, thereby effecting an application of the active ingredient of 280 grams per acre. At the end of a 12 week period, the crop is harvested and compared to another acre of the same field which has been sprayed with water simultaneously with the spraying of the test field to serve as a control. The results are shown below:

|  | CONTROL | TREATED SOYBEANS |
|---|---|---|
| Weight (Grams) of 100 Seeds | 15.3 | 14.7 |
| Pods per plant (Avg.) | 138 | 167 |
| Seeds per plant (Avg.) | 276 | 334 |
| Yield (Bushels per acre) | 45.4 | 57.1 |

It can be seen from the above that the application of the plant growth regulant effects a 26 percent increase in the yield of the soybeans.

EXAMPLE 2

120 soybeans (Kanrich) are grown in a greenhouse in 4.5 inch pots having about 2 inches of soil with four plants per pot. The temperature is maintained at standard greenhouse conditions: 70° to 85° F., with a peak summertime temperature of 95° F. Concentrates are prepared by dissolving a measured weight of a selected plant growth regulant in 25 milliliters of a solvent having the volume percent composition: 90% acetone, 8% methanol and 2% dimethylformamide. The selected plant growth regulants for which concentrates are prepared are methyl 6-nitro-2-oximinohexanoate, ethyl 6-nitro-2-oximinohexanoate and 6-nitro-2-oximinohexanamide. Three separate concentrates are prepared for each of the above plant growth regulants so that the measured weight of the selected plant growth regulants in the above solvent is 240, 60 and 15 grams.

Each growth regulant solution is evenly applied as a spray to 12 of the untreated soybean plants at the primary leaf stage, thereby effecting an application of the selected growth regulant of about 20, 5 and 1.25 milligrams per plant of active ingredient in the case of solutions containing 240, 60 and 15 grams of plant growth regulant, respectively. A group of 12 untreated soybean plants are sprayed with water to serve as control.

At the end of a 31 day period, the plant height of the soybeans are observed and are found to be as tabulated below:

| NITRO-OXIMINO ALKANATE | SOYBEAN HEIGHT (CENTIMETERS) AT INDICATED MILLIGRAM PER PLANT APPLICATION | | |
|---|---|---|---|
|  | 20 | 5 | 1.25 |
| Methyl 6-nitro-2-oximino-hexanoate | 10 | 17 | 40 |
| Ethyl 6-nitro-2-oximino-hexanoate | 9 | 18 | 31 |
| 6-nitro-2-oximinohexanamide | 22 | 30 | 39 |

The average height of the untreated soybean plants serving as control is observed to be 53 centimeters.

Thus, the application of the nitro-oximino hexanoic acid derivatives to the soybeans when compared with the untreated controls effects from 24 to 83 percent lowering of the plant height, and thereby produces soybean plants which due to their tendency to remain upright are harvested without the substantive yield loss which accompanies the harvesting of taller plants.

We claim:

1. A method for increasing the yield of plants which comprises applying to the plants an effective amount of a nitro-oximino alkanoic derivative having the general formula:

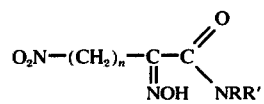

wherein $n$ is an integer from 1 to 12 and R and R' are independently selected from the group consisting of hydrogen, alkyl of 1–12 carbon atoms, cycloalkyl of 3–12 carbon atoms, hydrocarbyl aralkyl of 7–19 carbon atoms, hydrocarbyl alkaryl of 7–19 carbon atoms, hydrocarbyl aryl, alkenyl of 3–12 carbon atoms and alkynyl of 3–12 carbon atoms.

2. The method of claim 1 wherein R and R' are independently selected from the group consisting of hydrogen, alkyl of 1–12 carbon atoms, cycloalkyl of 3–12 carbon atoms, alkenyl of 3–12 carbon atoms and alkynyl of 3–12 carbon atoms.

3. The method of claim 1 wherein R and R' are independently selected from the group consisting of hydrocarbyl aralkyl of 7–19 carbon atoms, hydrocarbyl alkaryl of 7–19 carbon atoms and hydrocarbyl aryl.

4. The method of claim 1 wherein R and R' are each hydrogen.

5. The method of claim 4 wherein the nitro oximino alkanoic derivative is 6-nitro-2-oximinohexanamide.

6. The method of claim 1 wherein the plants are crop plants.

7. The method of claim 6 wherein the crop plants are legumes.

8. The method of claim 7 wherein the nitro-oximino alkanoic derivative is applied to the plant between the period of early flowering and early maturation of the fruit.

* * * * *